(12) United States Patent
Simpson et al.

(10) Patent No.: US 8,946,655 B2
(45) Date of Patent: Feb. 3, 2015

(54) MULTIPHOTON LUMINESCENCE IMAGING OF PROTEIN CRYSTALS

(75) Inventors: Garth J. Simpson, West Lafayette, IN (US); Ellen J. Gualtieri, Westborough, MA (US); David J. Kissick, Lafayette, IN (US); Jeremy Madden, Hillsboro, OR (US)

(73) Assignee: Purdue Research Foundation, West Lafayette, IN (US)

( * ) Notice: Subject to any disclaimer, the term of this patent is extended or adjusted under 35 U.S.C. 154(b) by 339 days.

(21) Appl. No.: 13/498,523

(22) PCT Filed: Sep. 27, 2010

(86) PCT No.: PCT/US2010/050409
§ 371 (c)(1),
(2), (4) Date: Jun. 7, 2012

(87) PCT Pub. No.: WO2011/038349
PCT Pub. Date: Mar. 31, 2011

(65) Prior Publication Data
US 2012/0241647 A1    Sep. 27, 2012

Related U.S. Application Data

(60) Provisional application No. 61/246,334, filed on Sep. 28, 2009.

(51) Int. Cl.
*G01N 21/64* (2006.01)
(52) U.S. Cl.
CPC ........ *G01N 21/6486* (2013.01); *G01N 21/6402* (2013.01); *G01N 21/6458* (2013.01)
USPC ..................................... 250/459.1

(58) Field of Classification Search
USPC ............................. 250/458.1, 459.1
See application file for complete search history.

(56) References Cited

U.S. PATENT DOCUMENTS

| | | | |
|---|---|---|---|
| 4,162,851 A | 7/1979 | Wada | |
| 7,256,894 B2 | 8/2007 | Chen et al. | |
| 7,329,880 B2 | 2/2008 | Kubo | |
| 2005/0237522 A1 | 10/2005 | Swift et al. | |
| 2006/0222220 A1 | 10/2006 | Yamano et al. | |
| 2006/0266954 A1 | 11/2006 | Sato et al. | |
| 2010/0039642 A1* | 2/2010 | Bahatt et al. | 356/328 |

FOREIGN PATENT DOCUMENTS

| | | |
|---|---|---|
| JP | 07035687 | 2/1995 |
| JP | 2007254415 | 10/2007 |

OTHER PUBLICATIONS

Wampler, R. D., D. J. Kissick, C. J. Dehen, E. J. Gualtieri, J. L. Grey, H.-F. Wang, D. H. Thompson, J.-X. Cheng, and G. Simpson, J. 2008. Nonlinear optical imaging of protein crsytallization. Selective Detection of Protein Crystals by Second Harmonic Microscopy, J. Amer. Chem. Soc. 130:14076-14077.

(Continued)

*Primary Examiner* — Mark R Gaworecki
(74) *Attorney, Agent, or Firm* — Brinks Gilson & Lione

(57) ABSTRACT

A method for detecting protein crystals comprises: illuminating a sample with a laser to produce multiphoton excitation; collecting an emission spectrum; and determining whether the sample comprises protein crystals.

18 Claims, 8 Drawing Sheets

(56) References Cited

OTHER PUBLICATIONS del Mercato, L. L., P. P. Pompa, G. Maruccio, A. Della Torre, S. Sabella, A. M. Tamburro, R. Cingolani, and R. Rinaldi. 2007. Charge transport and intrinsic fluorescence in amyloid-like fibrils. Proc. Natl. Acad. Sci. U. S. A. 104:18019-18024.

Guptasarma, P. 2008. Solution-state characteristics of the ultraviolet A-induced visible fluorescence from proteins. Archives of Biochemistry and Biophysics 478:127-129.

Shukla, A., S. Mukherjee, S. Sharma, V. Agrawal, K. V. Radha Kishan, and P. Guptasarma. 2004. A novel UV laser-induced visible blue radiation from protein crystals and aggregates: scattering artifacts or fluorescence transitions of peptide electrons delocalized through hydrogen bonding? Archives of Biochemistry and Biophysics 428:144-153.

Rosenberger, F., P. G. Vekilov, M. Muschol, and B. R. Thomas. Nucleation and crystallization of globular proteins—What we know and what is missing; Nov. 12-17, 1995; Hiroshima, Japan. Elsevier Science bv. p. 1-27.

Judge, R. A., R. S. Jacobs, T. Frazier, E. H. Snell, and M. L. Pusey. 1999. The effect of temperature and solution pH on the nucleation of tetragonal lysozyme crystals. Biophysical Journal 77:1585-1593.

Sangwal, K. 1996. Effects of impurities on crystal growth processes. Progress in Crystal Growth and Characterization of Materials 32:3-43.

Onoshima, Daisuke and Toyoko Imae, Dendritic nano- and microhydrogels fabricated by triethoxysilyl focal dendrons, eight pages, Dec. 6, 2005.

Asanov, A. N., H. M. McDonald, P. B. Oldham, M. J. Jedrzejas, and W. W. Wilson. Intrinsic fluorescence as a potential rapid scoring tool for protein crystals; May 14-19, 2000; Sandestin, Florida. p. 603-609.

Vernede, X., B. Lavault, J. Ohana, D. Nurizzo, J. Joly, L. Jacquamet, F. Felisaz, F. Cipriani, and D. Bourgeois. 2006. UV laser-excited fluorescence as a tool for the visualization of protein crystals mounted in loops. Acta Crystallographica Section D-Biological Crystallography 62:253-261.

Judge, R. A., K. Swift, and C. Gonzalez. 2005. An ultraviolet fluorescence-based method for identifying and distinguishing protein crystals. Acta Crystallographica Section D-Biological Crystallography 61:60-66.

Pohl, E., U. Ristau, T. Gehrmann, D. Jahn, B. Robrahn, D. Malthan, H. Dobler, and C. Hermes. 2004. Automation of the EMBL Hamburg protein crystallography beamline BW7B. Journal of Synchrotron Radiation 11:372-377.

Chan, K. L. A., L. Govada, R. M. Bill, N. E. Chayen, and S. G. Kazarian. 2009. Attenuated Total Reflection-FT-IR Spectroscopic Imaging of Protein Crystallization. Analytical Chemistry 81:3769-3775.

Groves, M. R., I. B. Muller, X. Kreplin, and J. Muller-Dieckmann. 2007. A method for the general identification of protein crystals in crystallization experiments using a noncovalent fluorescent dye. Acta Crystallographica Section D-Biological Crystallography 63:526-535.

Chu, C. C. and T. Imae. 2009. Fluorescence Investigations of Oxygen-Doped Simple Amine Compared with Fluorescent PAMAM Dendrimer. Macromolecular Rapid Communications 30:89-93.

Lee, W. I., Y. J. Bae, and A. J. Bard. 2004. Strong blue photoluminescence and ECL from OH-terminated PAMAM dendrimers in the absence of gold nanoparticles. Journal of the American Chemical Society 126:8358-8359.

Wang, D. J. and T. Imae. 2004. Fluorescence emission from dendrimers and its pH dependence. Journal of the American Chemical Society 126:13204-13205.

Wu, D. C., Y. Liu, C. B. He, and S. H. Goh. 2005. Blue photoluminescence from hyperbranched poly(amino ester)s. Macromolecules 38:9906-9909.

Antharjanam, P. K. S., M. Jaseer, K. N. Ragi, and E. Prasad. 2009. Intrinsic luminescence properties of ionic liquid crystals based on PAMAM and PPI dendrimers. Journal of Photochemistry and Photobiology a-Chemistry 203:50-55.

Jeong, S., G. Kwak, A. Takagi, M. Fujiki, D. H. Lee, L. S. Park, and K. B. Yoon. 2008. Luminous, fully aliphatic polyamides: Multicolor photoluminescence, their pH and solvent dependency. European Polymer Journal 44:1149-1156.

Lin, Y., J. W. Gao, H. W. Liu, and Y. S. Li. 2009. Synthesis and Characterization of Hyperbranched Poly(ether amide)s with Thermoresponsive Property and Unexpected Strong Blue Photoluminescence. Macromolecules 42:3237-3246.

Tamano, K. and T. Imae. 2008. Investigation of Luminescent Poly(propylene imine) Dendrimer. Journal of Nanoscience and Nanotechnology 8:4329-4334.

Mohamed, N. A. and M. M. Fahmy. 2009. Synthesis and Characterization of Novel Wholly Para-Oriented Aromatic Polyamide-Hydrazides Containing Sulfone-Ether Linkages. Journal of Applied Polymer Science 113:767-776.

Larson, J. M. 2006. The Nikon C1si combines high spectral resolution, high sensitivity, and high acquisition speed. Cytometry Part A 69A:825-834.

Durbin, S. D. and G. Feher. 1996. Protein crystallization. Annual Review of Physical Chemistry 47:171-204.

Skouri, M., B. Lorber, R. Giege, J. P. Munch, and J. S. Candau. 1995. Effect of Macromolecular Impurities on Lysozyme Solubility and Crystallizability—Dynamic Light-Scattering, Phase-diagram, and Crystal-growth Studies. Journal of Crystal Growth 152:209-220.

Vekilov, P. G. and F. Rosenberger. 1998. Protein crystal growth under forced solution flow: experimental setup and general response of lysozyme. Journal of Crystal Growth 186:251-261.

Hirschler, J. and J. C. FontecillaCamps. 1997. Protein crystal growth rates are face-specifically modified by structurally related contaminants. Journal of Crystal Growth 171:559-565.

Judge, R. A., E. L. Forsythe, and M. L. Pusey. 1998. The effect of protein impurities on lysozyme crystal growth. Biotechnology and Bioengineering 59:776-785.

Thomas, B. R., D. Carter, and F. Rosenberger. 1998. Effect of microheterogeneity on horse spleen apoferritin crystallization. Journal of Crystal Growth 187:499-510.

Matsui, T., G. Sazaki, H. Hondoh, Y. Matsuura, T. Nakada, and K. Nakajima. 2006. Impurity effects of lysozyme molecules specifically labeled with a fluorescent reagent on the crystallization of tetragonal and monoclinic lysozyme crystals. Journal of Crystal Growth 293:415-422.

Burke, M. W., R. Leardi, R. A. Judge, and M. L. Pusey. 2001. Quantifying main trends in lysozyme nucleation: The effect of precipitant concentration, supersaturation, and impurities. Crystal Growth & Design 1:333-337.

Asherie, N., C. Ginsberg, A. Greenbaum, S. Blass, and S. Knafo. Effects of Protein Purity and Precipitant Stereochemistry on the Crystallization of Thaumatin; May 6-8, 2008; Cancun City, Mexico. Amer Chemical Soc. p. 4200-4207.

Dobrianov, I., C. Caylor, S. G. Lemay, K. D. Finkelstein, and R. E. Thorne. X-ray diffraction studies of protein crystal disorder; May 3-8, 1998; Granada, Spain. Elsevier Science bv. p. 511-523.

Van Driessche, A. E. S., G. Sazaki, G. L. Dai, F. Otalora, J. A. Gavira, T. Matsui, I. Yoshizaki, K. Tsukamoto, and K. Nakajima. 2009. Direct Observation of Adsorption Sites of Protein Impurities and Their Effects on Step Advancement of Protein Crystals. Crystal Growth & Design 9:3062-3071.

Carter, D. C., K. Lim, J. X. Ho, B. S. Wright, P. D. Twigg, T. Y. Miller, J. Chapman, K. Keeling, J. Ruble, P. G. Vekilov, B. R. Thomas, F. Rosenberger, and A. A. Chernov. Lower dimer impurity incorporation may result in higher perfection of HEWL crystals grown in microgravity—A case study; May 3-8, 1998; Granada, Spain. Elsevier Science bv. p. 623-637.

Robert, M. C., B. Capelle, B. Lorber, and R. Giege. Influence of impurities on protein crystal perfection; May 14-19, 2000; Sandestin, Florida. Elsevier Science bv. p. 489-497.

Yoshizaki, I., S. Fukuyama, H. Koizumi, M. Tachibana, K. Kojima, Y. Matsuura, M. Tanakae, N. Igarashi, A. Kadowaki, L. Rong, S. Adachi, S. Yoda, and H. Komatsu. 2006. Impurity-induced defect and its effect on protein crystal perfection. Journal of Crystal Growth 290:185-191.

(56) References Cited

OTHER PUBLICATIONS

Caylor, C. L., I. Dobrianov, S. G. Lemay, C. Kimmer, S. Kriminski, K. D. Finkelstein, W. Zipfel, W. W. Webb, B. R. Thomas, A. A. Chernov, and R. E. Thorne. 1999. Macromolecular impurities and disorder in protein crystals. Proteins-Structure Function and Genetics 36:270-281.

Wampler, R. D., D. J. Kissick, C. J. Dehen, E. J. Gualtieri, J. L. Grey, H.-F. Wang, D. H. Thompson, J.-X. Cheng, and G. Simpson, J. 2008. J. Amer. Chem. Soc. 130; Selective Detection of Protein Crystals by Second Harmonic Microscopy. p. 14076-14077.

Extended European Search Report, European Application No. / Patent No. 10819608.0/1554 / 2483665 PCT/US2010050409, dated Jul. 22, 2013, 11 pages.

Alexander J. Malkin et al., "Growth and disorder of macromolecular crystals: insights from atomic force microscopy and X-ray diffraction studies," Methods, vol. 34, 2004, pp. 273-299.

\* cited by examiner

MULTIPHOTON LUMINESCENCE IMAGING OF PROTEIN CRYSTALS

CROSS-REFERENCE TO RELATED APPLICATION AND INCORPORATION BY REFERENCE

The present application is the U.S. national phase application of PCT Application No. PCT/US2010/050409, filed Sep. 27, 2010, which claims priority to U.S. Provisional Patent Application No. 61/246,334, filed Sep. 28, 2009, the entirety of both of which is hereby incorporated by reference.

All listed references are hereby incorporated by reference.

FIELD OF THE INVENTION

The present disclosure relates to a protein crystal detection method, more specifically to a method of multiphoton excited luminescence imaging of protein crystals.

BACKGROUND OF THE INVENTION

Protein structure determination is a key step in developing molecular-level understandings of the role of proteins in cell signaling pathways, which in turn can guide understanding of diseases and the rational design of potential drugs for treatment. High-resolution structures of relatively large proteins are generally obtained by X-ray diffraction from protein crystals. Consequently, identification of the conditions amenable to the formation of diffraction-quality protein crystals remains a major bottleneck in the sequence to structure pipeline. Because of the large chemical space associated with finding the appropriate crystallization conditions, it is routine to perform hundreds of crystallization trials for a given protein target. High throughput approaches for rapidly preparing and screening large numbers of crystallization trials have improved the pace of structure-discovery, increasingly placing the bottleneck for protein structure determination on the development of reliable and automated methods for protein crystal detection for efficiently mapping and sampling chemical space.

Numerous strategies have been adopted for selectively and rapidly identifying protein crystals. The simplest experimental approaches rely on visual inspection or algorithmic analysis of bright-field images, which can be error-prone (high false-positive/false negative rates) and particularly challenging for small (<5 μm) crystals. UV fluorescence of intrinsic aromatic residues is also widely used, offering improved image contrast and facile discrimination between protein crystals and small-molecule crystals of salts or other additives in the mother liquor. However, the deep uv excitation light used for intrinsic UV fluorescence exhibits poor transparency in conventional optical elements and most polymeric materials used for crystallization screenings, posing practical limitations on its general applicability. Furthermore, UV fluorescence cannot easily discriminate between disordered aggregates and microcrystalline conglomerates. Moreover, the high-energy photons used for UV-imaging (<280 nm) can induce photochemical damage to proteins during long or repeated exposures through the breakage of disulfide bonds and polymerization of neighboring residues within the crystalline lattice. The use of attenuated total reflection FT-IR spectroscopic imaging of protein crystallizations has recently been demonstrated as a technique that can distinguish between protein and precipitant crystals. Although this technique has the ability to selectively image protein crystals through the protein-specific amide bond at 1550 $cm^{-1}$, it is difficult to implement on traditional crystallization screening platforms, such as 96 well plates, thus making it a limited and specialized technique. Other techniques for discriminating between protein and precipitant protein crystals are the "crush test" where the crystals are deemed protein if they disintegrate when touched with a needle and the staining of crystals with Coommasie Brilliant Blue dye, both of which are destructive techniques. More recently, second order nonlinear optical imaging of chiral crystals (SONICC) based on second harmonic generation (SHG) microscopy has been shown to be highly selective for protein crystal detection. Coherent SHG only arises from assemblies with long-range order, allowing selective identification of protein crystals with negligible contributions from solvated proteins or amorphous aggregates.

Although SONICC remains an attractive option, one alternative approach to shift the fluorescence of protein crystals to the visible region of the spectrum is to incorporate organic fluorophores into protein crystals at low doping densities by addition to the mother liquor. Although the degree of incorporation within the crystalline lattice can vary substantially depending on the nature of the fluorophore and the protein, the resulting fluorescence intensity of the crystal will often be higher than the surrounding mother liquor by nature of the higher local density. Furthermore, low doping densities have the advantage of suppressing autoquenching, which can substantially reduce the overall quantum efficiency for emission of intrinsic chromophores (e.g., tryptophan). A major disadvantage of fluorophore doping is that protein crystals can routinely exhibit low or moderate doping efficiencies, with the fluorescence from solvated dye increasing the background and reducing image contrast.

Detection of intrinsic visible light emission from native, unlabeled protein crystals can reduce complications associated with incorporation of large organic chromophores while still maintaining compatibility with conventional optical components and detectors. Intrinsic one-photon excited emission of visible light has been reported in previous studies of seemingly innocuous organic assemblies lacking obvious chromophores, including proteinacious material, triethylamine, poly(amido amine) dendrimers, aliphatic polyamides, poly(ether amide)s, poly(propylene imine), and poly (amine-amide)s. In those studies, a combination of fluorescence and phosphorescence was observed, with oxygen implicated as a critical component, possibly through oxygen exiplex formation with amino groups. This mechanism suggests that visible emission could potentially be observed in broad classes of organic species.

BRIEF SUMMARY OF THE INVENTION

In one aspect, a method for detecting protein crystals comprises: illuminating a sample with a laser to produce multiphoton excitation; collecting an emission spectrum; and determining whether the sample comprises protein crystals.

In another aspect, a method for detecting protein crystals, comprising: illuminating a sample with a laser to produce multiphoton excitation; obtaining an image of the sample; and determining whether the sample comprises protein crystals.

In yet another aspect, a method for imaging a macromolecule, comprising: illuminating a sample with a laser to produce multiphoton excitation; obtaining an image of the sample.

BRIEF DESCRIPTION OF THE DRAWINGS

FIG. 4a is a brightfield image of UCH-L1 protein crystals.

FIG. 4b is a one-photon excited visible emission image of the sample of FIG. 4a.

FIG. 4c is a brightfield image of thaumatin crystals.

FIG. 4d is a one-photon excited visible emission image of the sample of FIG. 4c.

DETAILED DESCRIPTION OF THE DISCLOSURE

Figures 1A, 1B, 1E, 1F:
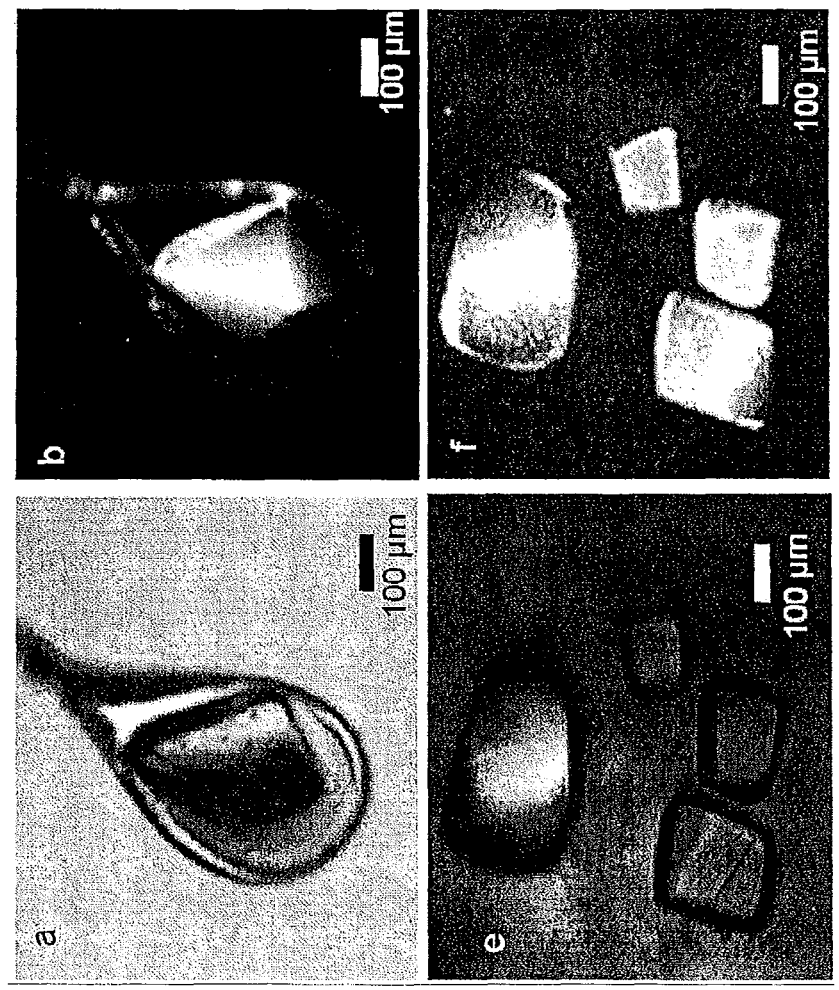
FIG. 1a is a brightfield image of thaumatin in a nylon loop.
FIG. 1b is a two-photon excited image of the sample of FIG. 1a, according to one embodiment of the present disclosure.
FIG. 1e is a brightfield image of SOD protein crystals.
FIG. 1f is a two-photon excited image of the sample of FIG. 1e according to one embodiment of the present disclosure.

The present disclosure provides a method of detection and imaging protein crystals. In particular, multiphoton excited luminescence is employed for selective detection and imaging of protein crystals. The method includes illuminating a sample with a laser; collecting an emission spectrum, evaluating the spectrum, and determining whether the sample contains protein crystals. Preferably, the sample is excited by simultaneous absorption of two or more photons. More preferably, the sample is excited by simultaneous absorption of two or three photons. Preferably, the known spectra of protein crystals are used to evaluate the observed spectrum, and therefore identify the presence of protein crystals.

The present method can detect any suitable protein crystals, such as super-oxide dismutases (SODs), lysozyme, insulin, myoglobin, deubiquitinating enzymes, and combinations thereof. The method also can be used to image polymers, such as polyamides, amino-dendrimers, etc.

The instrument of the present disclosure can be any suitable microscope that can produce two or more photons excitation. Preferably, a confocal microscope is used. Preferably, the laser is generated from a femtosecond laser source. More preferably, the laser source is a Ti:Sapphire laser source.

The laser can be in the ultraviolet, visible, or infrared range. Preferably, the laser has a wavelength in the visible or infrared range. More preferably, the laser has a wavelength of about 515 nm, or about 800 nm.

In some embodiments of the present disclosure, the emission spectrum is in the visible range. The spectrum is a luminescence emission spectrum. In some embodiments, the spectrum is a fluorescence emission spectrum. Preferably, a three-dimensional excitation and emission spectrum is collected.

In some embodiments, the images of the sample are captured and observed to determine whether the sample contains protein crystals. The image is a luminescence image. In some embodiments, the image is a fluorescence image.

Although the ubiquitous observation of visible light emission preferentially from protein crystals has notable practical benefits as a complement to existing protein crystal detection methods, the molecular nature of the emitting species is not immediately obvious when excited outside of the wavelength range for aromatic amino acid absorption. Resolving the molecular origin of the emission can provide a predictive framework for interpreting imaging contrast. The absorption and emission wavelengths are well outside of the range for accessing aromatic amino acid residues (e.g., tryptophan, tyrosine, etc.). As such, it is difficult to explain the observed ubiquitous visible emission in terms of conventional conjugated aromatic groups attached to the main protein chain.

Without wishing to be bound by any theory, several emission mechanisms have been postulated. Visible emission could potentially arise from the incorporation and concentration of trace impurities into the crystalline lattice. Impurities have been shown to substantially impact nucleation, growth rates, and crystal quality. However, the observation of remarkably similar luminescence spectra from crystals for different proteins is not directly consistent with trace impurities, unless such impurities are likely to appear ubiquitously in protein crystal preparations. Furthermore, the emission spectra from protein crystals are nearly identical to those from the polyamide nylon loops, despite the fundamental differences in structure, processing, and materials properties. Similar emission spectra have also been reported for amino-dendrites, and triethylamine, suggesting a common origin for the relatively bright visible luminescence from diverse organic molecules and macromolecules. Given the radically different synthetic pathways used to generate each species, it is highly unlikely that similar impurities are present in each of these different samples.

Several hypotheses have been forwarded for the origin of the intrinsic photoemission observed primarily in molecular constructs containing sterically hindered amino-groups. In previous studies with poly(amido amine) dendrimers, oxygen has been shown to be important for promoting visible-light excited luminescence. This finding is initially somewhat counter-intuitive, as oxygen is also a well-known fluorescence and phosphorescence quenching agent through energy transfer to the triplet state. The fact that bright, long-lived luminescence with similar emission spectra has been observed in polyamides, amino-dendrimers, and molecules as simple as triethylamine suggests that the effect is not limited to particular proteins or substituents (e.g., aromatic amino acid residues), and may well be responsible for luminescence in broad classes of amino-containing species, including the amide backbones of proteins. Consequently, it may well serve as a general and selective method for protein crystal detection.

The absence of luminescence from the closely packed salt crystals supports the hypothesis of oxygen driven luminescent mechanism where tightly packed crystalline arrays such as salts will not luminescence due to the inability of oxygen to diffuse through the crystalline lattice.

DETAILED DESCRIPTION OF PREFERRED EMBODIMENTS

Other features of the present disclosure will become apparent from the following discussion of the preferred embodiments, which is illustrated in the accompanying drawings. The components in the figures are not necessarily to scale, emphasis instead being placed upon illustrating the principles of the invention. Moreover, in the figures, referenced numerals designate corresponding parts throughout the different views.

Experimental Methods

UCHL1, SOD and thaumatin protein crystals were prepared via standard vapor diffusion protocols. Wild type UCHL1 was expressed as a glutathione S-transferase (GST) fusion protein and was purified on a glutathione-Sepharose column (GE Biosciences) using manufacturer's instructions. Crystals were grown using the hanging drop vapor diffusion method from a solution that contained 2.4 M ammonium sulfate and 0.1 M HEPES (pH 7.0). The S134N mutant of human SOD1 (hereafter referred to as SOD1S134N) was subcloned into the pGEX-6P1 vector (GE Biosciences) using standard cloning protocols. The resulting GST-tagged construct was expressed in Rosetta *E. coli* strain and was purified on a glutathione-Sepharose column (GE Biosciences) using manufacturer's instructions. The protein was further purified by size exclusion chromatography using a Superdex S75 column (GE Biosciences). Crystals of SOD1S134N were grown using the hanging drop vapor diffusion method from a solution that contained 2.0 M ammonium sulfate, 0.1 M tri-sodium citrate dihydrate (pH 5.6) and 0.2 M potassium sodium tartrate tetrahydrate. Thaumatin purchased from Sigma (Lot #T7638) was crystallized via vapor diffusion in a hanging drop. A 30 mg/mL solution of thaumatin dissolved in dionized water was mixed in 1:1 ratio with 0.5 M sodium potassium tartrate in dionized water and crystallized in a hanging drop.

Two-photon excited luminescence images were acquired using a custom built confocal microscope performing beam scanning with a resonant vibrating mirror (7.8 kHz) directing the laser beam along the fast scan axis and a mirror galvanometer for sample-scanning along the slow axis. The incident beam was generated from a Spectra-Physics Mai Tai, approximately 100 femtosecond, 80 MHz, 100 mW average power at 800 nm focused onto the sample with a 10× (0.3 N.A.) objective. Multialkali PMTs (Burle, XP29290PC) were used to collect the visible luminescence generated in the epi direction with a band-pass filter from 450-570 nm (Omega, 3rd 450-570) and a dichroic mirror to reject the incident beam. Emission spectra were also acquired in the epi-generated direction through a monochromator (Acton Research Spectra Pro 150, 1200 groves/mm, blaze angle for 500 nm) and detected with a photomultiplier tube (PMT).

A laser scanning confocal microscope equipped with a 32-channel multi-anode photomultiplier tube array (Nikon A1) was used to acquire one-photon excited visible emission images and spectra. The 405 nm incident light was focused onto the sample with a 10× objective (0.3 numerical aperture) and emission from 408-710 nm was collected on the multi-anode PMT array.

An Olympus BX51 microscope was used for conventional one-photon excitation with a 10× (0.3 numerical aperture) objective. Images were acquired with blue excitation from 460-490 nm and detection in the green from 520-800 nm with a CCD camera (Olympus DP71).

Two-photon excited intrinsic fluorescence images were acquired using similar instrumentation as two-photon excited luminescence images, where a Nikon TE2000 microscope was used as a base. Beam scanning was completed with a resonant vibrating mirror (8.8 kHz) and a mirror galvanometer for fast and slow scan axis. The incident beam was generated by doubling the incident light to 515 nm, approximately 300 femtosecond, 5 mW, generated by a Polaronyz Uranus laser, approximately 200 femtosecond, 50 mW average power, 76 MHz, focused onto the sample with a 10× (0.3N.A.) objective. With UV excitation occurring at 257.5 nm at the sample, the signal, at around 350 nm, was collected in the trans-direction by a bialkali PMT (Hamamatsu, R1924), through a bandpass filter from 350 to 370 nm (Chroma, HQ360-20m), a 514 nm notch filter (Chroma), and a dichoric to reject the fundamental beam.

Figure 1C:
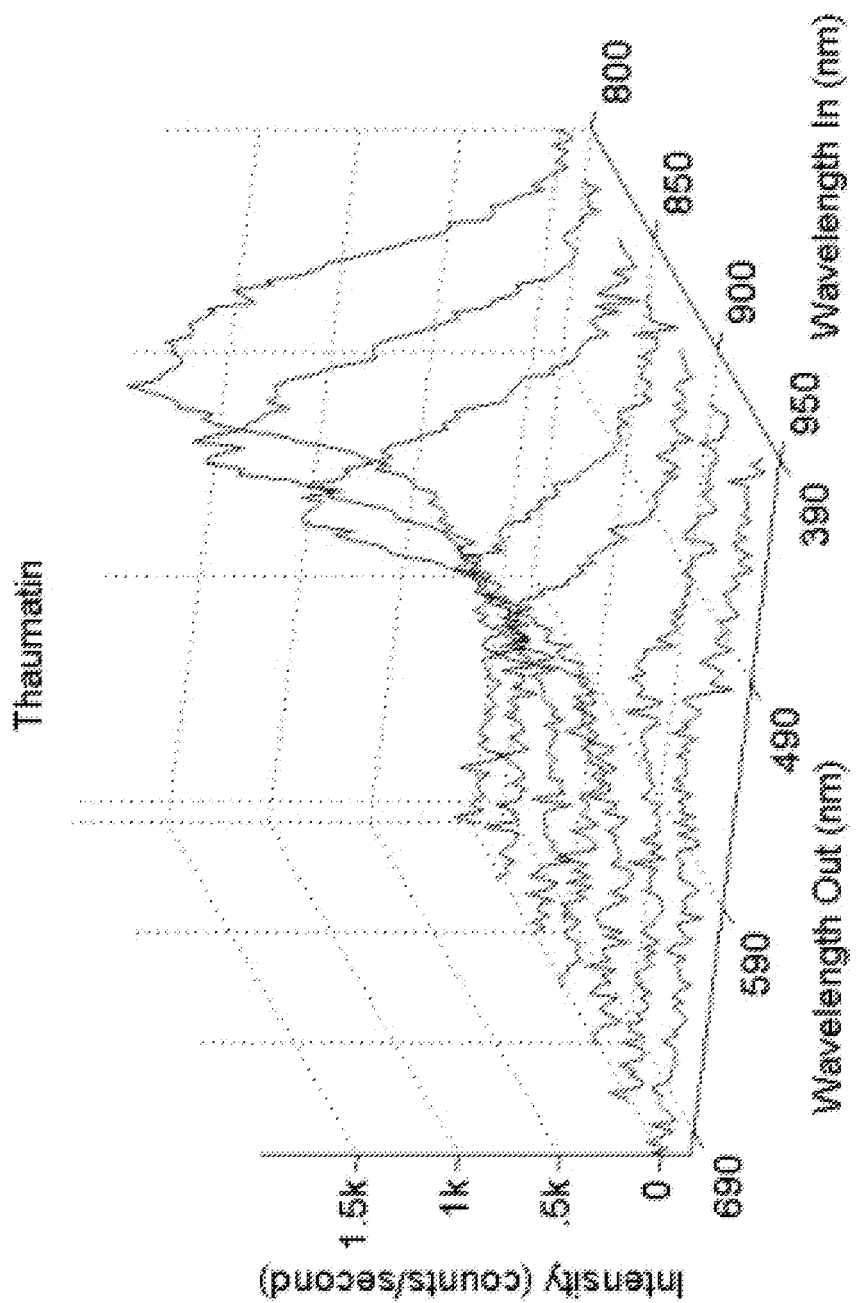
FIG. 1c is a graph of the two-photon excited emission spectra of thaumatin according to one embodiment of the present disclosure.
Figure 1D:
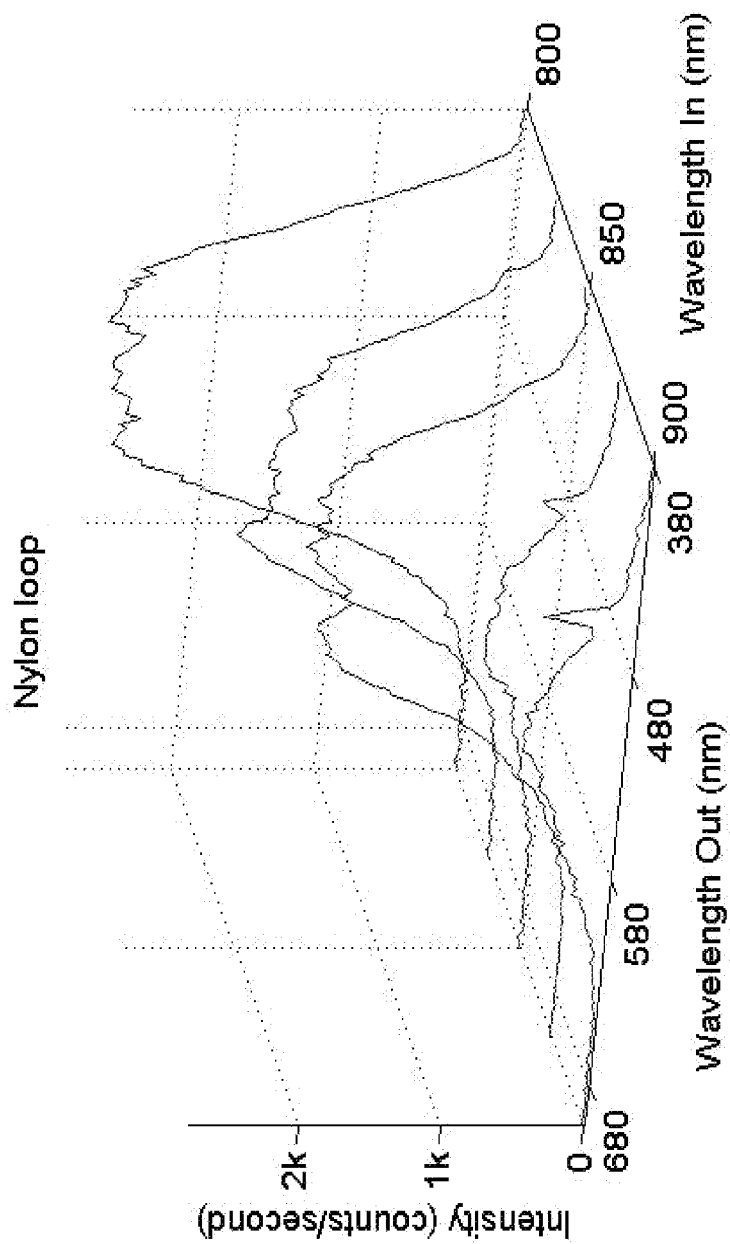
FIG. 1d is a graph of the emission spectra of the Nylon loop according to one embodiment of the present disclosure.
Figure 1G:
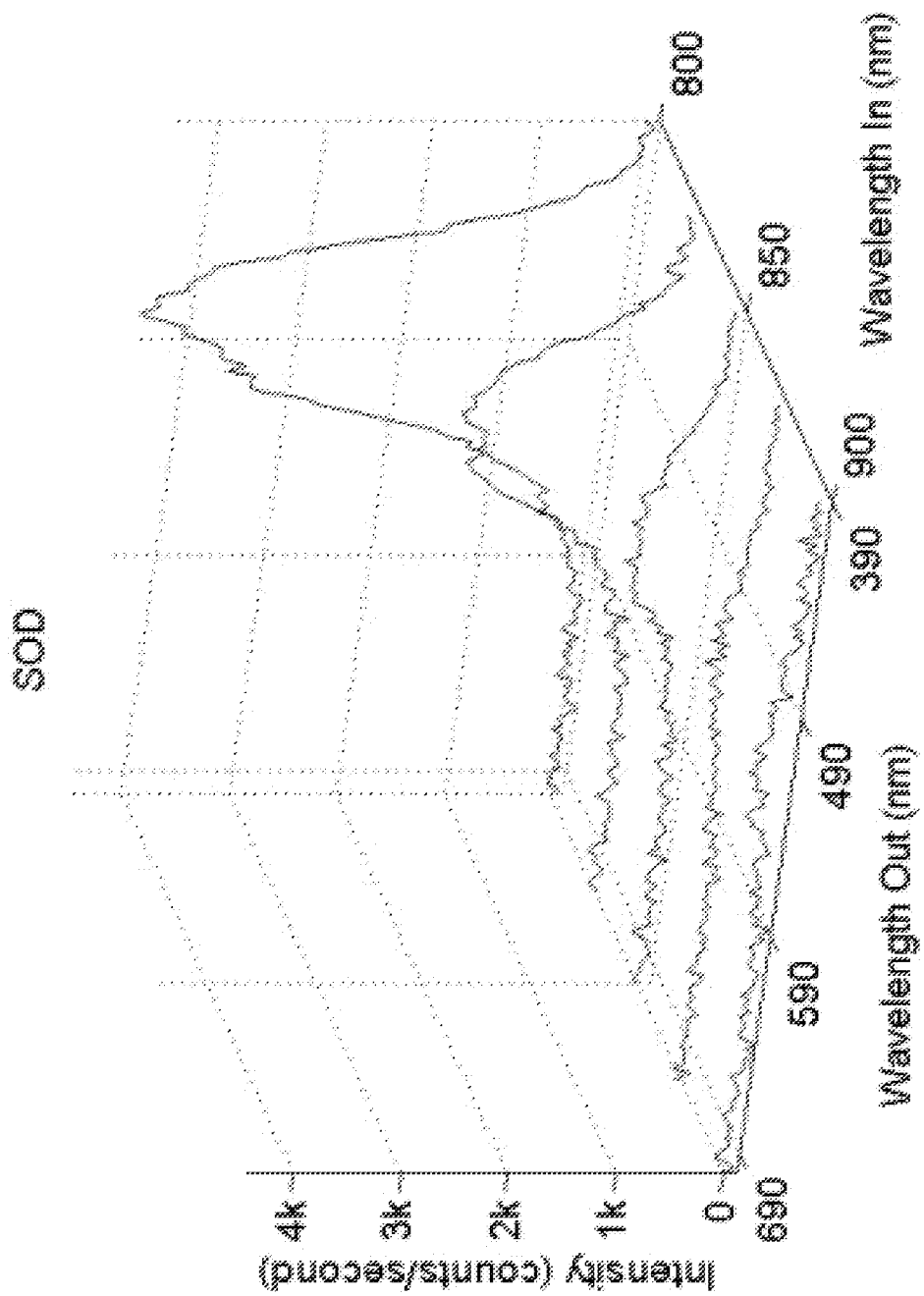
FIG. 1g is a graph of the emission spectra of SOD protein crystals according to one embodiment of the present disclosure.
Figures 2A, 2B:
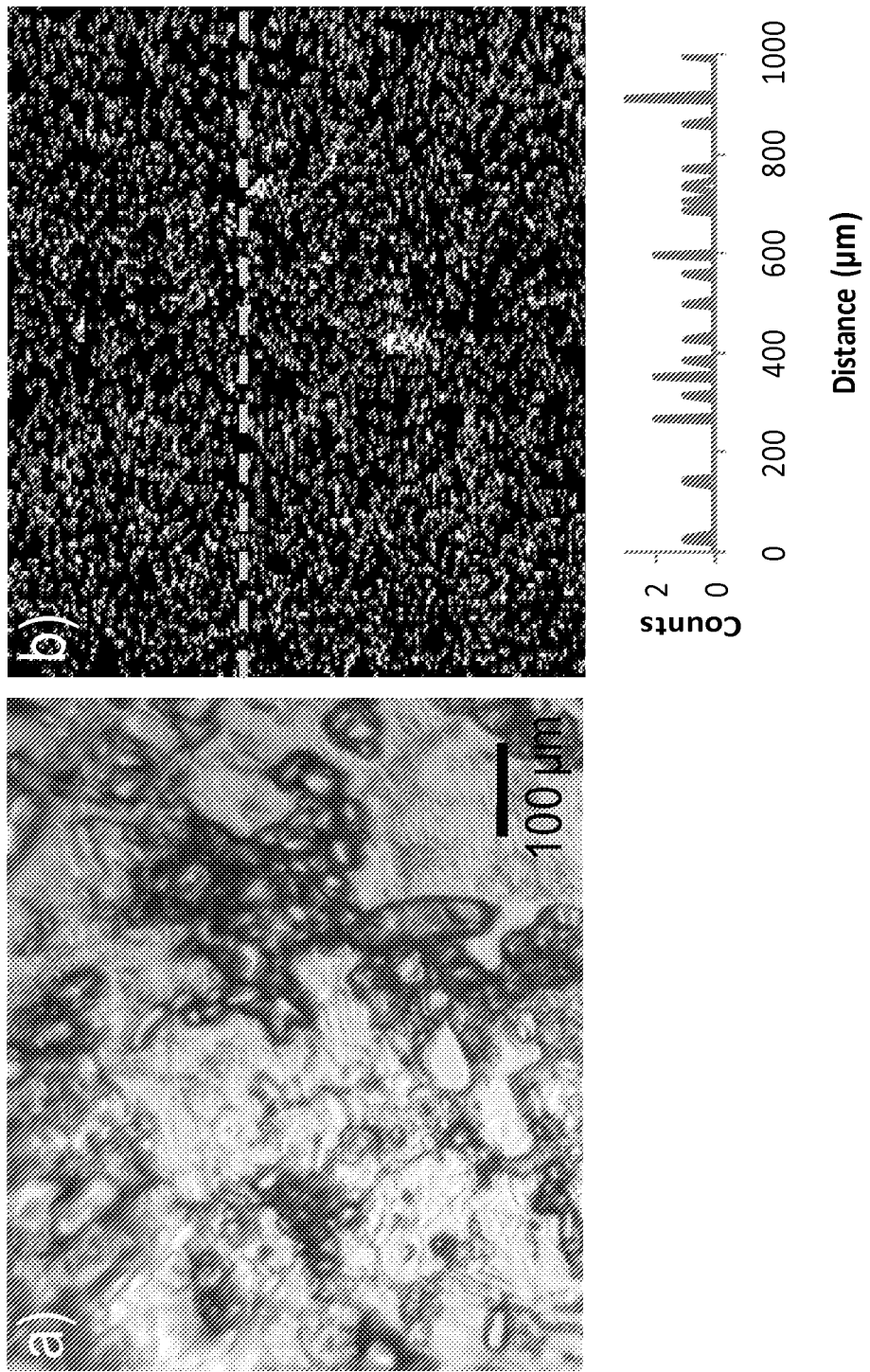
FIG. 2a is a brightfield image of ammonium sulfate crystals.
FIG. 2b is a corresponding transmission generated SHG and line trace.

Two-photon excited visible luminescence images for crystals of thaumatin and a super-oxide dismutase (SOD) mutant are shown in FIGS. 1*b* and 1*f*, along with the corresponding emission spectra FIGS. 1*c* and 1*g*. As a comparison, conventional brightfield images of thaumatin and SOD are shown in FIGS. 1*a* and 1*e*. Two-photon excited luminescence images were acquired with a 80 MHz femtosecond Ti:Sapphire laser operating at 800 nm with the epi-generated luminescence collected through a filter (450 nm to 570 nm). Emission spectra were acquired in the epi-generated direction through a monochromator. Similar broad-band emission spectra were observed in both cases, extending from the two-photon energy of 400 nm out to 600 nm (FIGS. 1*c* and 1*g*). Visible luminescence has also been observed in other protein crystals including lysozyme, insulin, and myoglobin. The emission spectra from the polyamide nylon loop (FIG. 1*d*) coincide with the spectra from the protein crystals. In contrast, no detectable luminescence was observed for ammonium sulfate crystals (FIG. 2) under similar imaging conditions.

Figures 3A, 3B, 3C:
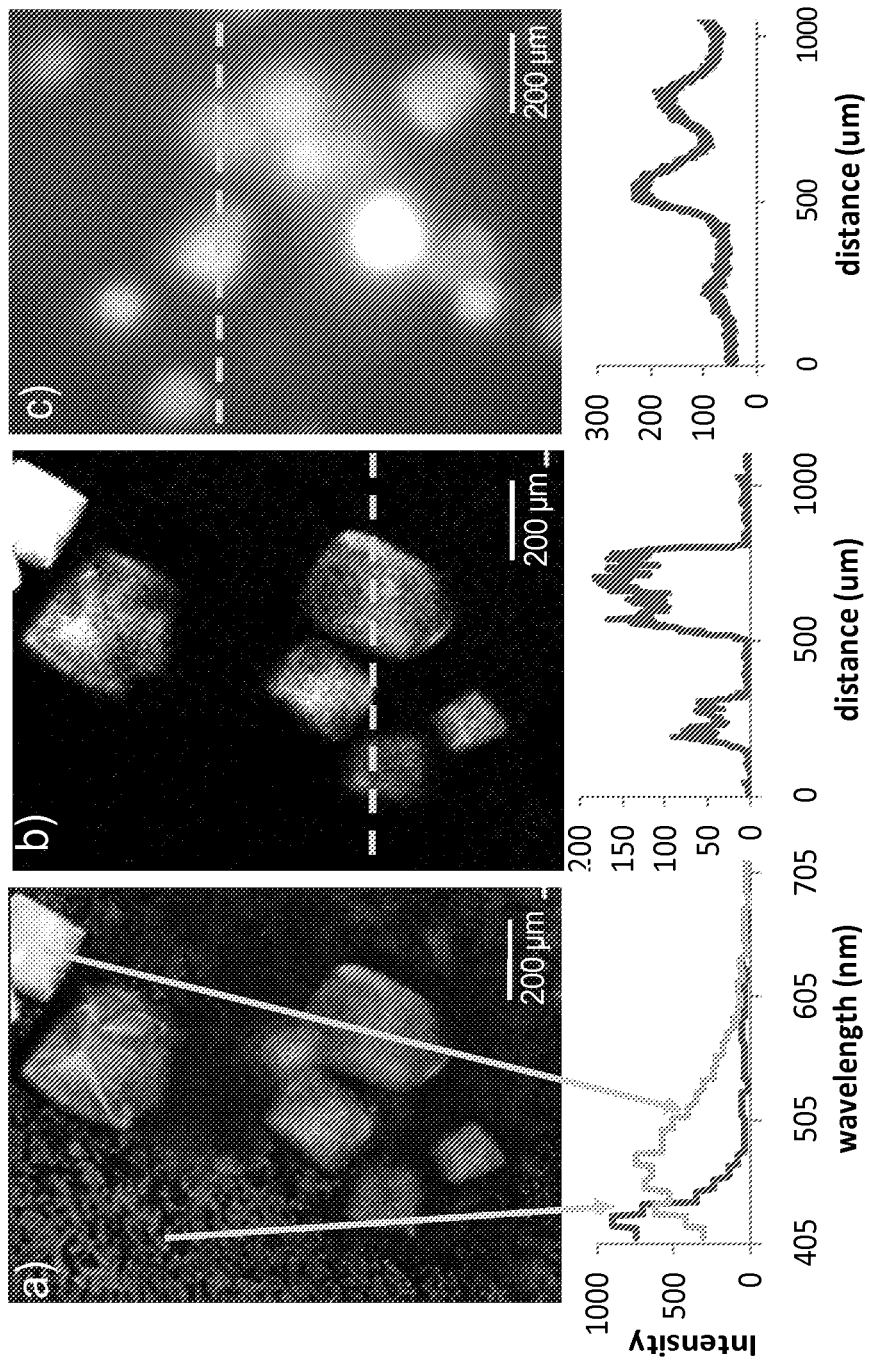
FIG. 3a is a one photon laser-scanned excited confocal emission image of SOD protein aggregates and crystals at the wavelengths of 408-710 nm with corresponding emission profiles from the aggregates and crystal.
FIG. 3b is a one photon laser-scanned excited confocal emission image of SOD protein crystals at the wavelengths of 408-710 nm with corresponding crystal emission profile.
FIG. 3c is a one photon laser-scanned excited confocal emission image of SOD protein aggregate at the wavelengths of 408-710 nm with corresponding aggregate emission profile.

Contrast for protein crystal detection can also be observed using conventional one-photon excitation for UCH-L1 (FIGS. 3*a* and 3*b*), a deubiquitinating enzyme of the ubiquitin C-terminal hydrolase (UCH) family, and thaumatin (FIG. 3*c*) by wide-field fluorescence imaging. Images were acquired using blue excitation from 460-490 nm and detection in the green from 520-800 nm.

Figures 4A, 4B, 4C, 4D:
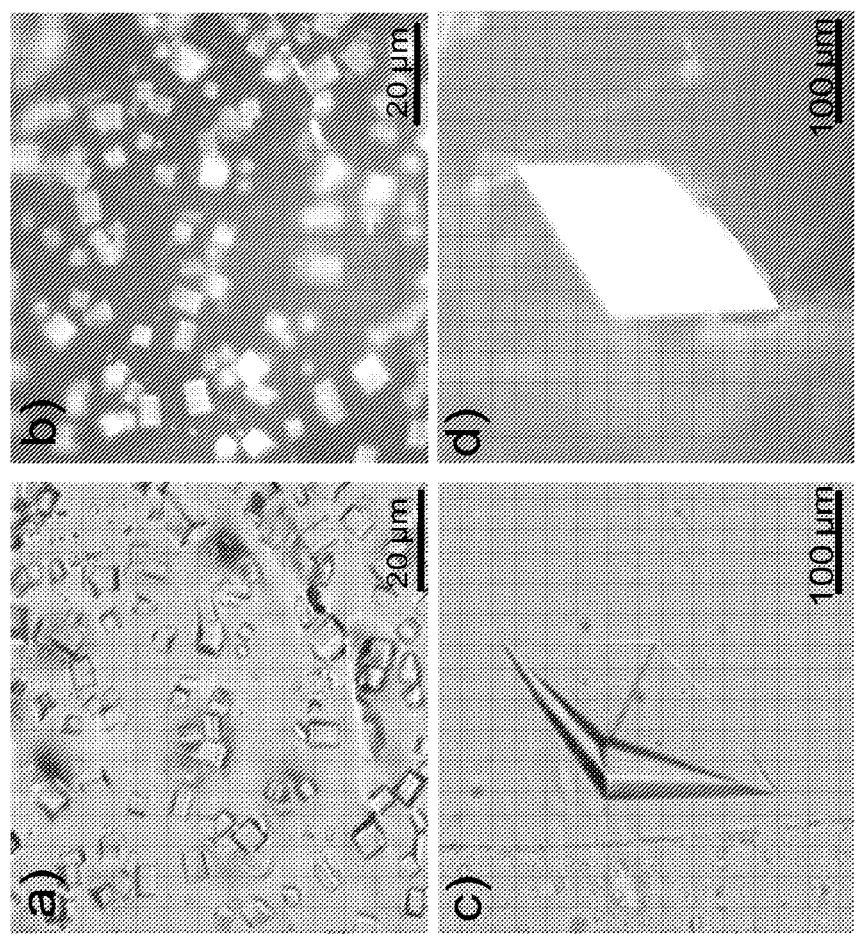

One-photon excited visible luminescence images of SOD crystals acquired using a laser scanning confocal microscope equipped with a 32-channel multi-anode photomultiplier tube array (Nikon A1) are shown in FIGS. 4*a*-4*d*. The integrated intensity image of the combined luminescence detected from 408 nm to 705 nm (405 nm excitation) is shown in FIG. 4*a*. Although little detectable fluorescence was observed from the bulk solution, visible luminescence was readily observed from both crystals and aggregates, with the crystals producing a significantly greater red-shifted emission compared to the aggregates. Numerical separation based on a proprietary unmixing algorithm employed in the Nikon A1 software utilizing the least squares method with linear regression allowed selective identification of the protein crystal from the emission spectra. Unmixing of the luminescence spectra at each pixel generated two images corresponding to the crystals (FIG. 4*b*) and aggregates. A line trace of the SOD crystals in FIG. 4b shows the ability to detect protein crystals with high selectivity and without significant interference from aggregates. Comparison to deep UV excited images of SOD crystals (FIG. 4c) shows similar contrast but with a much higher background, presumably arising from fluorescence generated by solvated and/or aggregated protein.

Figures 5A, 5B:
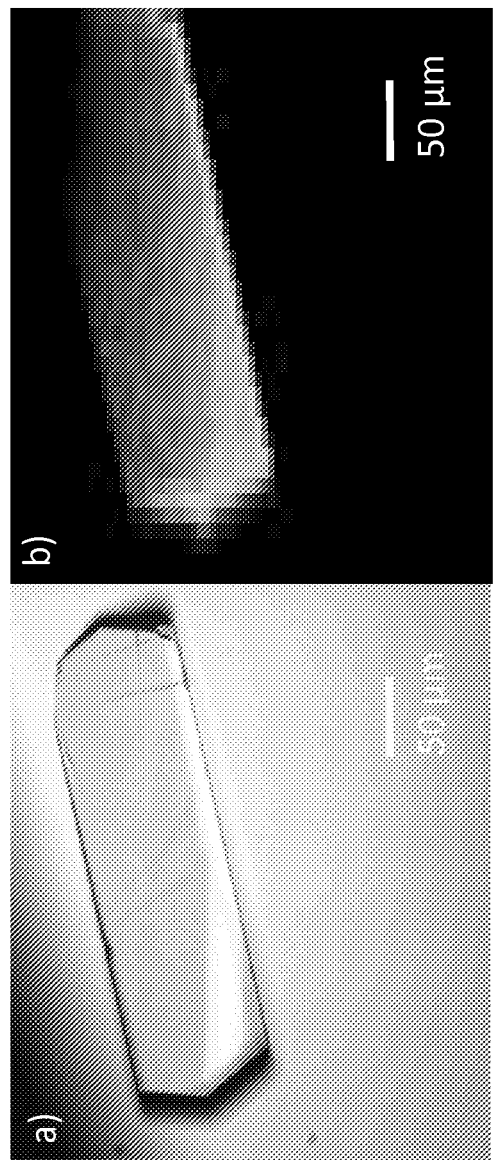
FIG. 5a is a brightfield image of a lysozyme crystal.
FIG. 5b is a two-photon excited visible emission (350-370 nm) image of a lysozyme protein crystal when excited at 515 nm according to one embodiment of the present disclosure.

Conventional brightfield image of a lysozyme crystal is shown in FIG. 5a. A two-photon excited image of the same sample is shown in FIG. 5b. The protein crystal was excited with a 515 nm femtosecond laser and the fluorescence emission collected in the transmission direction at 350-370 nm corresponding to the emission of tryptophan and tyrosine. Two-photon excitation of the aromatic amino acid residues is advantageous in that conventional optics can be utilized and also that there is no out of plane damage to the proteins.

Many modifications and other embodiments of the present disclosure will come to mind to one skilled in the art to which the present disclosure pertains having the benefit of the teachings presented in the foregoing description. It will be apparent to those skilled in the art that variations and modifications of the present disclosure may be made without departing from the scope or spirit of the present disclosure. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

REFERENCES

1. Asanov, A. N., H. M. McDonald, P. B. Oldham, M. J. Jedrzejas, and W. W. Wilson. Intrinsic fluorescence as a potential rapid scoring tool for protein crystals; 2000 May 14-19; Sandestin, Fla. p 603-609.
2. Vernede, X., B. Lavault, J. Ohana, D. Nurizzo, J. Joly, L. Jacquamet, F. Felisaz, F. Cipriani, and D. Bourgeois. 2006. UV laser-excited fluorescence as a tool for the visualization of protein crystals mounted in loops. Acta Crystallographica Section D-Biological Crystallography 62:253-261.
3. Judge, R. A., K. Swift, and C. Gonzalez. 2005. An ultraviolet fluorescence-based method for identifying and distinguishing protein crystals. Acta Crystallographica Section D-Biological Crystallography 61:60-66.
4. Pohl, E., U. Ristau, T. Gehrmann, D. Jahn, B. Robrahn, D. Malthan, H. Dobler, and C. Hermes. 2004. Automation of the EMBL Hamburg protein crystallography beamline BW7B. Journal of Synchrotron Radiation 11:372-377.
5. Chan, K. L. A., L. Govada, R. M. Bill, N. E. Chayen, and S. G. Kazarian. 2009. Attenuated Total Reflection-FT-IR Spectroscopic Imaging of Protein Crystallization. Analytical Chemistry 81:3769-3775.
6. Wampler, R. D., D. J. Kissick, C. J. Dehen, E. J. Gualtieri, J. L. Grey, H.-F. Wang, D. H. Thompson, J.-X. Cheng, and G. Simpson, J. 2008. Nonlinear optical imaging of protein crsytallization. J. Amer. Chem. Soc. 130:14076-14077.
7. Groves, M. R., I. B. Muller, X. Kreplin, and J. Muller-Dieckmann. 2007. A method for the general identification of protein crystals in crystallization experiments using a noncovalent fluorescent dye. Acta Crystallographica Section D-Biological Crystallography 63:526-535.
8. del Mercato, L. L., P. P. Pompa, G. Maruccio, A. Della Torre, S. Sabella, A. M. Tamburro, R. Cingolani, and R. Rinaldi. 2007. Charge transport and intrinsic fluorescence in amyloid-like fibrils. Proc. Natl. Acad. Sci. U.S.A. 104: 18019-18024.
9. Guptasarma, P. 2008. Solution-state characteristics of the ultraviolet A-induced visible fluorescence from proteins. Archives of Biochemistry and Biophysics 478:127-129.
10. Shukla, A., S. Mukherjee, S. Sharma, V. Agrawal, K. V. Radha Kishan, and P. Guptasarma. 2004. A novel UV laser-induced visible blue radiation from protein crystals and aggregates: scattering artifacts or fluorescence transitions of peptide electrons delocalized through hydrogen bonding? Archives of Biochemistry and Biophysics 428: 144-153.
11. Chu, C. C. and T. Imae. 2009. Fluorescence Investigations of Oxygen-Doped Simple Amine Compared with Fluorescent PAMAM Dendrimer. Macromolecular Rapid Communications 30:89-93.
12. Lee, W. I., Y. J. Bae, and A. J. Bard. 2004. Strong blue photoluminescence and ECL from OH-terminated PAMAM dendrimers in the absence of gold nanoparticles. Journal of the American Chemical Society 126:8358-8359.
13. Wang, D. J. and T. Imae. 2004. Fluorescence emission from dendrimers and its pH dependence. Journal of the American Chemical Society 126:13204-13205.
14. Wu, D. C., Y. Liu, C. B. He, and S. H. Goh. 2005. Blue photoluminescence from hyperbranched poly(amino ester)s. Macromolecules 38:9906-9909.
15. Onoshima, D. and T. Imae. 2006. Dendritic nano- and microhydrogels fabricated by triethoxysilyl focal dendrons. Soft Matter 2:141-148.
16. Antharjanam, P. K. S., M. Jaseer, K. N. Ragi, and E. Prasad. 2009. Intrinsic luminescence properties of ionic liquid crystals based on PAMAM and PPI dendrimers. Journal of Photochemistry and Photobiology a-Chemistry 203:50-55.
17. Jeong, S., G. Kwak, A. Takagi, M. Fujiki, D. H. Lee, L. S. Park, and K. B. Yoon. 2008. Luminous, fully aliphatic polyamides: Multicolor photoluminescence, their pH and solvent dependency. European Polymer Journal 44:1149-1156.
18. Lin, Y., J. W. Gao, H. W. Liu, and Y. S. Li. 2009. Synthesis and Characterization of Hyperbranched Poly(ether amide)s with Thermoresponsive Property and Unexpected Strong Blue Photoluminescence. Macromolecules 42:3237-3246.
19. Tamano, K. and T. Imae. 2008. Investigation of Luminescent Poly(propylene imine) Dendrimer. Journal of Nanoscience and Nanotechnology 8:4329-4334.
20. Mohamed, N. A. and M. M. Fahmy. 2009. Synthesis and Characterization of Novel Wholly Para-Oriented Aromatic Polyamide-Hydrazides Containing Sulfone-Ether Linkages. Journal of Applied Polymer Science 113:767-776.
21. Larson, J. M. 2006. The Nikon C1si combines high spectral resolution, high sensitivity, and high acquisition speed. Cytometry Part A 69A:825-834.
22. Rosenberger, F., P. G. Vekilov, M. Muschol, and B. R. Thomas. Nucleation and crystallization of globular proteins—What we know and what is missing; 1995 Nov. 12-17; Hiroshima, Japan. Elsevier Science Bv. p 1-27.
23. Durbin, S. D. and G. Feher. 1996. Protein crystallization. Annual Review of Physical Chemistry 47:171-204.
24. Skouri, M., B. Lorber, R. Giege, J. P. Munch, and J. S. Candau. 1995. Effect of Macromolecular Impurities on Lysozyme Solubility and Crystallizability—Dynamic Light-Scattering, Phase-diagram, And Crystal-growth Studies. Journal of Crystal Growth 152:209-220.
25. Judge, R. A., R. S. Jacobs, T. Frazier, E. H. Snell, and M. L. Pusey. 1999. The effect of temperature and solution pH on the nucleation of tetragonal lysozyme crystals. Biophysical Journal 77:1585-1593.

26. Sangwal, K. 1996. Effects of impurities on crystal growth processes. Progress in Crystal Growth and Characterization of Materials 32:3-43.
27. Vekilov, P. G. and F. Rosenberger. 1998. Protein crystal growth under forced solution flow: experimental setup and general response of lysozyme. Journal of Crystal Growth 186:251-261.
28. Hirschler, J. and J. C. FontecillaCamps. 1997. Protein crystal growth rates are face-specifically modified by structurally related contaminants. Journal of Crystal Growth 171:559-565.
29. Judge, R. A., E. L. Forsythe, and M. L. Pusey. 1998. The effect of protein impurities on lysozyme crystal growth. Biotechnology and Bioengineering 59:776-785.
30. Thomas, B. R., D. Carter, and F. Rosenberger. 1998. Effect of microheterogeneity on horse spleen apoferritin crystallization. Journal of Crystal Growth 187:499-510.
31. Matsui, T., G. Sazaki, H. Hondoh, Y. Matsuura, T. Nakada, and K. Nakajima. 2006. Impurity effects of lysozyme molecules specifically labeled with a fluorescent reagent on the crystallization of tetragonal and monoclinic lysozyme crystals. Journal of Crystal Growth 293:415-422.
32. Burke, M. W., R. Leardi, R. A. Judge, and M. L. Pusey. 2001. Quantifying main trends in lysozyme nucleation: The effect of precipitant concentration, supersaturation, and impurities. Crystal Growth & Design 1:333-337.
33. Asherie, N., C. Ginsberg, A. Greenbaum, S. Blass, and S. Knafo. Effects of Protein Purity and Precipitant Stereochemistry on the Crystallization of Thaumatin; 2008 May 6-8; Cancun City, MEXICO. Amer Chemical Soc. p 4200-4207.
34. Dobrianov, I., C. Caylor, S. G. Lemay, K. D. Finkelstein, and R. E. Thorne. X-ray diffraction studies of protein crystal disorder; 1998 May 3-8; Granada, Spain. Elsevier Science Bv. p 511-523.
35. Van Driessche, A. E. S., G. Sazaki, G. L. Dai, F. Otalora, J. A. Gavira, T. Matsui, I. Yoshizaki, K. Tsukamoto, and K. Nakajima. 2009. Direct Observation of Adsorption Sites of Protein Impurities and Their Effects on Step Advancement of Protein Crystals. Crystal Growth & Design 9:3062-3071.
36. Carter, D. C., K. Lim, J. X. Ho, B. S. Wright, P. D. Twigg, T. Y. Miller, J. Chapman, K. Keeling, J. Ruble, P. G. Vekilov, B. R. Thomas, F. Rosenberger, and A. A. Chernov. Lower dimer impurity incorporation may result in higher perfection of HEWL crystals grown in microgravity—A case study; 1998 May 3-8; Granada, Spain. Elsevier Science Bv. p 623-637.
37. Robert, M. C., B. Capelle, B. Lorber, and R. Giege. Influence of impurities on protein crystal perfection; 2000 May 14-19; Sandestin, Fla. Elsevier Science Bv. p 489-497.
38. Yoshizaki, I., S. Fukuyama, H. Koizumi, M. Tachibana, K. Kojima, Y. Matsuura, M. Tanakae, N. Igarashi, A. Kadowaki, L. Rong, S. Adachi, S. Yoda, and H. Komatsu. 2006. Impurity-induced defect and its effect on protein crystal perfection. Journal of Crystal Growth 290:185-191.
39. Caylor, C. L., I. Dobrianov, S. G. Lemay, C. Kimmer, S. Kriminski, K. D. Finkelstein, W. Zipfel, W. W. Webb, B. R. Thomas, A. A. Chernov, and R. E. Thorne. 1999. Macromolecular impurities and disorder in protein crystals. Proteins-Structure Function and Genetics 36:270-281.

What is claimed is:

1. A method for detecting protein crystals, comprising:
    illuminating a sample with a laser to produce multiphoton excitation;
    collecting an emission spectrum; and
    determining whether the sample comprises protein crystals.
2. The method of claim 1, wherein the excitation is a two-photon excitation.
3. The method of claim 1, wherein the laser has a wavelength in the visible range.
4. The method of claim 1, wherein the laser has a wavelength in the infrared range.
5. The method of claim 1, wherein the laser has a wavelength of about 800 nm.
6. The method of claim 1, wherein the laser has a wavelength of about 515 nm.
7. The method of claim 1, wherein the sample comprises a protein selected from the group consisting of super-oxide dismutases (SODs), thaumatin, lysozyme, insulin, myoglobin, deubiquitinating enzymes, and combinations thereof.
8. The method of claim 1, wherein the excitation is a three-photon excitation.
9. The method of claim 1, wherein the laser is generated from a femtosecond laser source.
10. The method of claim 1, wherein the laser source is a Ti:Sapphire laser source.
11. The method of claim 1, wherein the emission spectrum is a luminescence spectrum.
12. The method of claim 1, wherein the emission spectrum is a fluorescence spectrum.
13. The method of claim 1, wherein the emission is in the visible range.
14. The method of claim 1, wherein the determining comprises a step of comparing the collected spectrum with known spectra of protein crystals.
15. The method of claim 1, wherein the collected spectra are three-dimensional spectra.
16. A method for detecting protein crystals, comprising:
    illuminating a sample with a laser to produce multiphoton excitation;
    obtaining an image of the sample; and
    determining whether the sample comprises protein crystals.
17. The method of claim 16, wherein the image is a luminescence image.
18. The method of claim 16, wherein the image is a fluorescence image.

* * * * *